United States Patent [19]

Handy et al.

[11] Patent Number: 4,543,820
[45] Date of Patent: Oct. 1, 1985

[54] TAPERED BLADE IN SITU SOIL TESTING DEVICE

[75] Inventors: Richard L. Handy, Ames, Iowa; Alan J. Lutenegger, Potsdam, N.Y.

[73] Assignee: Iowa State University Research Foundation, Inc., Ames, Iowa

[21] Appl. No.: 611,125

[22] Filed: May 17, 1984

[51] Int. Cl.[4] ............................................. G01N 3/00
[52] U.S. Cl. ........................................... 73/84; 73/784
[58] Field of Search ............. 73/84, 432 SD, 73, 784, 73/37

[56] References Cited

U.S. PATENT DOCUMENTS

| | | | |
|---|---|---|---|
| 2,793,527 | 5/1957 | Turner, Jr. et al. | 73/73 |
| 2,957,341 | 10/1960 | Menard | 73/84 |
| 3,364,737 | 1/1968 | Comes | 73/84 |
| 3,427,876 | 2/1969 | Steele et al. | 73/784 X |
| 3,446,062 | 5/1969 | Goodman | 73/84 |
| 3,466,926 | 9/1969 | Ruppeneit et al. | 73/151 |
| 3,481,188 | 12/1969 | Mori | 73/84 |
| 3,499,320 | 3/1970 | Fox et al. | 73/84 |
| 3,572,114 | 3/1971 | Ruppeneit et al. | 73/784 X |
| 3,610,035 | 10/1971 | Handy | 73/84 |
| 3,906,781 | 9/1975 | Vlasblom | 73/84 |
| 3,988,923 | 11/1976 | Elmiger et al. | 73/84 |
| 4,043,186 | 8/1977 | Marchetti | 73/84 |
| 4,398,414 | 8/1983 | MacGregor | 73/84 |
| 4,445,788 | 5/1984 | Twersky et al. | 73/432 R |

*Primary Examiner*—Jerry W. Myracle
*Assistant Examiner*—Hezron Williams
*Attorney, Agent, or Firm*—Zarley, McKee, Thomte, Voorhees & Sease

[57] ABSTRACT

The soil testing device of the present invention includes a tapered body member having opposite tapered surfaces which converge toward one another at their lower ends. Within one of the tapered surfaces is a cavity having a diaphragm placed thereover. Beneath the diaphragm are a plurality of sensors which extend in a line between the upper and lower ends of the cavity. Means are provided for introducing fluid pressure into the cavity. When the device is inserted into the soil, the sensors sense the various pressures being exerted on the diaphragm by the soil, and record these pressures on a gauge or meter located above the surface of the soil.

10 Claims, 10 Drawing Figures

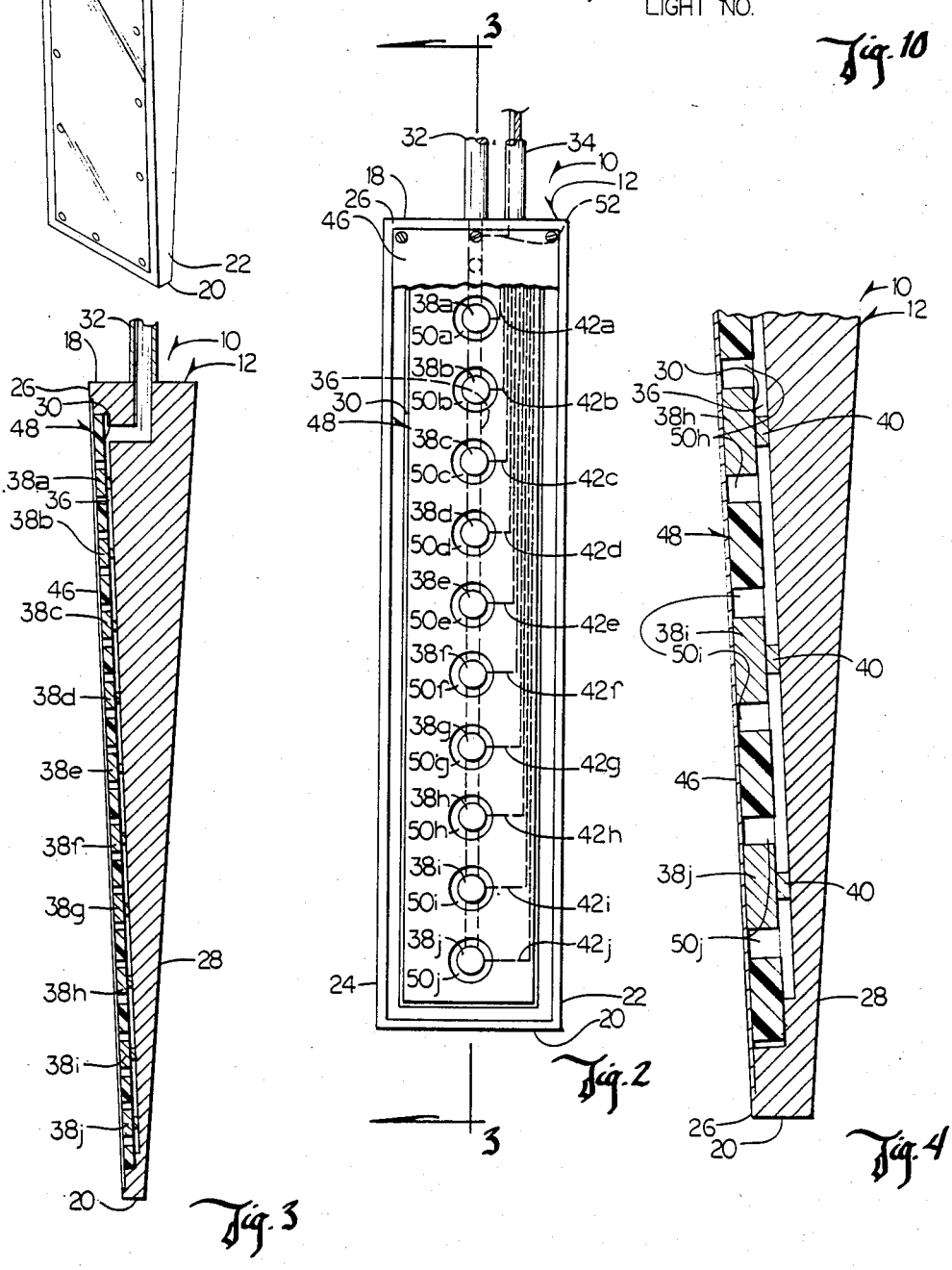

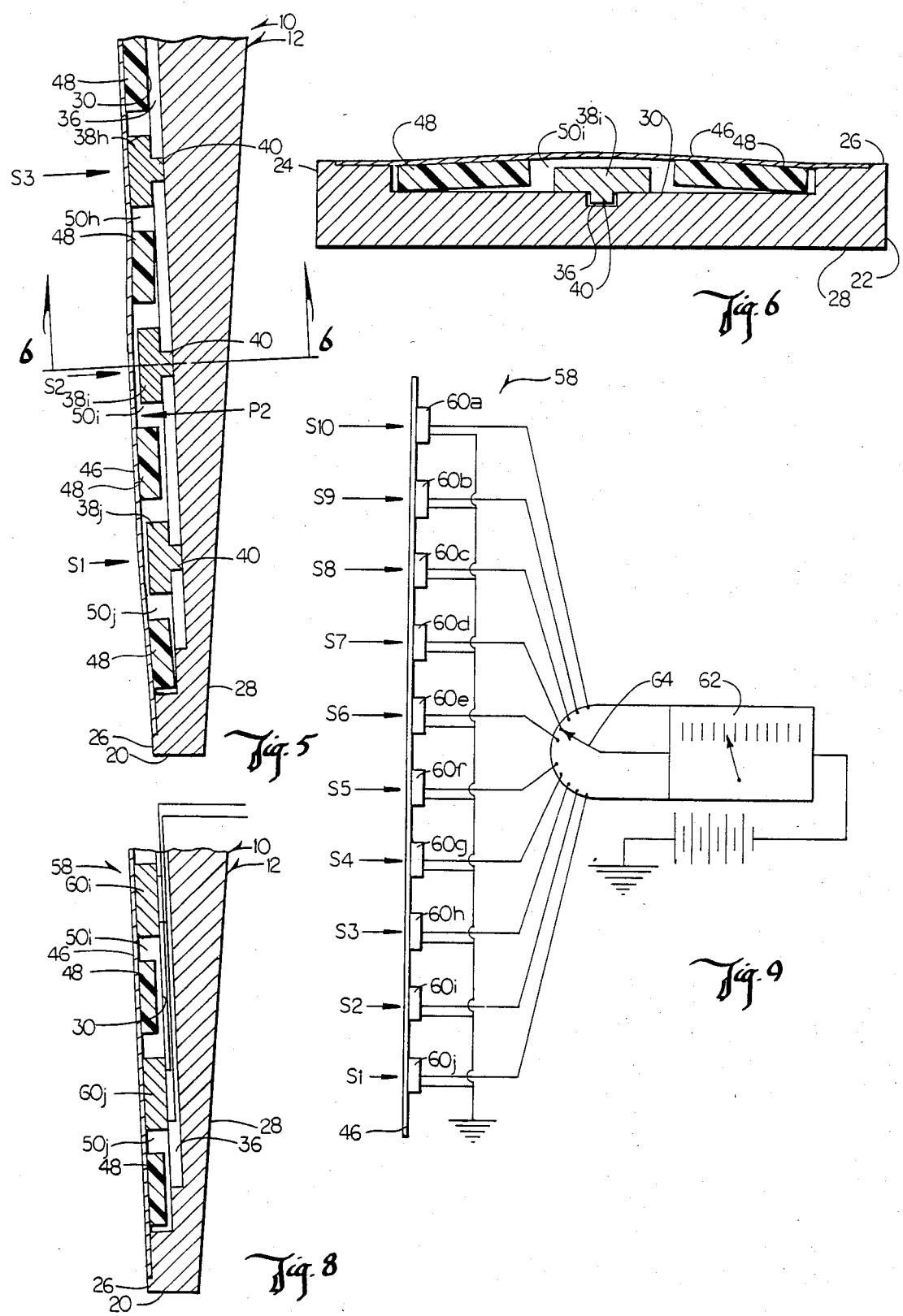

4,543,820

TAPERED BLADE IN SITU SOIL TESTING DEVICE

BACKGROUND OF THE INVENTION

This invention relates to an in situ soil testing device, and particularly a tapered in situ soil testing device for measuring in situ soil stresses and other properties.

Numerous devices have been used for testing the in situ stresses in the soil. One of these devices utilizes a multi-vaned blade which may be inserted into the soil. Strain gauges on the surfaces of the various blades measure the soil stresses or pressures which are exerted on the faces of the blade.

When blades of different thicknesses are used, the soil exerts correspondingly different stresses or pressures on the faces of the blades. Generally, the thicker the blade, the greater the soil pressure, and the thinner the blade, the less the soil pressure. However, in soft soils, a plastic failure may occur causing lower pressures to be recorded on the thicker portion of the wedge. The use of a tapered device, such as contemplated by the present invention, is to accurately define the pressure at which this behavior may occur and to give a multiplicity of data points for defining soil response to continuously increasing thickness of a penetrating wedge.

One method for analyzing the soil stress characteristics has been to insert blades of different thicknesses into the soil. The pressures on the faces of the blades are then measured and plotted on a graph. The X-axis of the graph reflects the blade thickness and the Y-axis of the graph reflects the logarithim of pressure reading obtained.

The points plotted in this manner will generally represent a straight line, which when extended to the Y-axis will reflect the theoretical soil pressure which would be obtained for a blade having zero thickness. This procedure is quite adequate for stiff soils, which exhibit high values of elastic modulus; however, softer soils which may behave plastically at low disturbance may cause problems with data interpretation.

Ideally, then, for testing soft soils, it would be desirable to increase the number of individual blades to generate more data points. However, such an approach involves substantial expense and furthermore does not result in an efficient tool for field use. Thus, the use of a multi-blade device has certain limitations and is not strictly applicable to testing soft soils.

Therefore, a primary object of the present invention is the provision of an improved in situ soil testing device.

A further object of the present invention is the provision of a device which permits the measurement of a plurality of soil pressures with a singular device.

A further object of the present invention is the provision of a device including a wedged surface having a plurality of pressure sensors along its length for reading the various soil pressures exerted on the wedged surface.

A further object of the present invention is the provision of a device giving an optimum number of individual thickness-pressure measurements so as to increase the reliability of the soil pressure readings taken with the device.

A further object of the present invention is the provision of a device which is simple in construction and can be easily used in the field.

A further object of the present invention is the provision of a device which is efficient in operation, durable in use and economical to manufacture.

SUMMARY OF THE INVENTION

The present invention utilizes a wedge shaped body member having opposite tapered surfaces. The wedge shaped body member has its largest thickness adjacent its upper end and its smallest thickness adjacent its lower end.

On one of the tapered surfaces of the wedge is formed a cavity which contains a plurality of sensors extending along the length thereof. A diaphragm is attached over the cavity to provide a fluid tight seal therewith. A fluid conduit provides communication to the interior of the cavity so that fluid pressure can be applied to the inside of the cavity.

Each of the individual sensors is connected to an indicator device adapted to be used above the ground. Also, a pressure gauge is attached to the fluid pressure conduit so as to register the fluid pressure within the cavity.

In use, the device is forced into the ground with the pointed part of the wedge positioned downwardly. The soil exerts pressure on the wedge, with the smallest amount of pressure being exerted adjacent the lower end of the wedge where the wedge is thinnest, and with the greatest soil pressure being exerted on the wedge at the upper end where the wedge is the thickest.

In one version of the invention, the sensors within the cavity are contacts which are in electrical contact with the diaphragm. After the wedge has been inserted into the ground, pressure is slowly introduced to the cavity so as to exert a force on the diaphragm which is directly opposite to the force being exerted by the soil against the diaphragm. The fluid pressure is slowly increased until it exceeds the soil pressure at the lower end of the diaphragm. In response to this imbalance of pressure, the diaphragm at the lower end of the wedge bulges outwardly and breaks electrical contact with the contact sensor at the lower end of the wedge. This causes the indicator to indicate that the contact at the lower end of the wedge has been broken. A suitable indicator for each contact is a light emitting diode which can be electrically connected thereto.

As the pressure is gradually increased, the contacts of the various sensors with the diaphragm are broken, commencing at the lower end of the wedge and progressively continuing upwardly to the upper end of the wedge.

By measuring the fluid pressure within the cavity at the time that each contact is broken, it is possible to plot a series of points on an X Y axis with the X axis representing the light emitting diode corresponding to each contact along the tapered wedge representing a different blade thickness along the wedge, and with the Y axis representing the pressure registered at the time the light emitting diode went out.

The various points plotted on the graph will generally represent a straight line which can be extended to the Y axis to show the pressure which would theoretically be exerted on a plate having a zero thickness.

In another version of the invention, strain gauges are used in the place of the contact sensors. Each strain gauge registers the pressure being exerted on the diaphragm, and is electrically connected to a meter which registers the soil pressure being exerted thereon. Individual meters may be provided for each strain gauge, or a switch may be used to connect the meter to each strain gauge separately and individually.

BRIEF DESCRIPTION OF THE FIGURES OF THE DRAWINGS

FIG. 1 is a perspective view of the device of the present invention.

FIG. 2 is a front plan view of the device, showing a portion of the diaphragm plate cut away.

FIG. 3 is a sectional view taken along line 3—3 of FIG. 2.

FIG. 4 is an enlarged detailed sectional view of the lower end of the device shown in FIG. 3.

FIG. 5 is a view similar to FIG. 4, but showing the lower end of the diaphragm bulged outwardly.

FIG. 6 is a sectional view taken along line 6—6 of FIG. 5.

FIG. 8 is a sectional view similar to the view shown in FIG. 5, but showing a modified form of the invention.

FIG. 9 is a schematic diagram of the device shown in FIG. 8.

FIG. 10 is a graph showing the pressure readings taken at the time each indicator light goes out.

DETAILED DESCRIPTION OF THE PREFERRED EMBODIMENT

Figure 7:
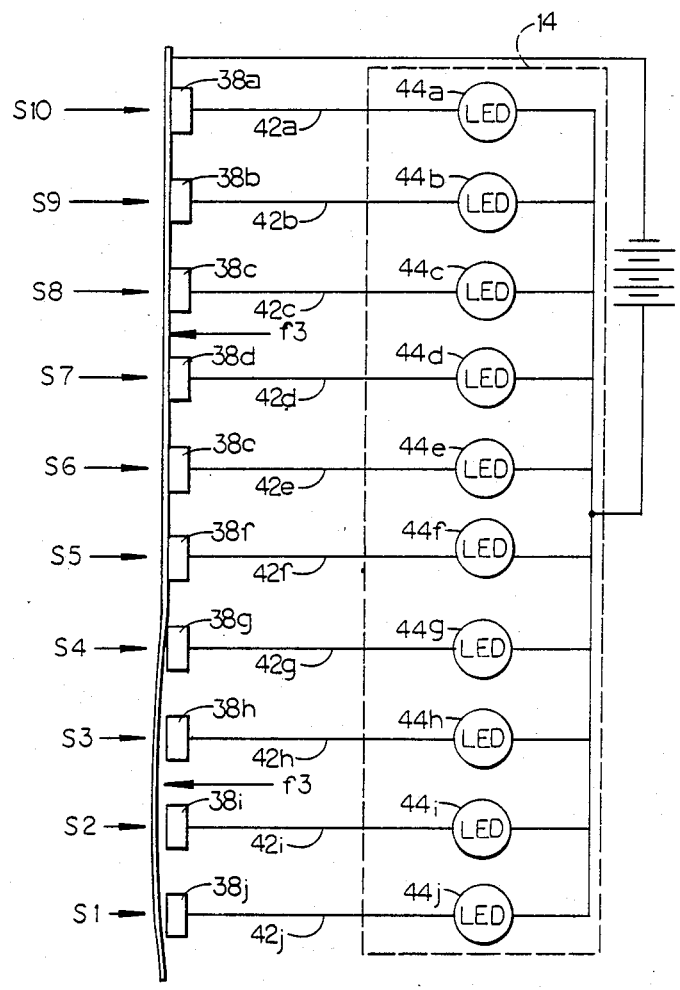
FIG. 7 is a schematic diagram of the device shown in FIGS. 1-6.

Referring to the drawings, the numeral 10 generally designates the soil testing device of the present invention. Device 10 includes a wedge shaped body member 12, a light indicator assembly 14, and a pressure gauge 16.

Wedge shaped body member 12 includes a top edge 18, a bottom edge 20, a pair of opposite side edges 22, 24 and a pair of opposite tapered surfaces 26, 28. Surface 26 is provided with a rectangular elongated cavity 30 which extends along the substantial length of tapered surface 26. A fluid conduit 32 provides communication from outside the body member 12 to the interior of cavity 30. Also in communication with the interior of cavity 30 is an electrical conduit 34. Extending along the length of the floor of cavity 30 is an elongated groove or channel 36, and this channel 36 is in communication with conduit 32, so that fluid can flow along groove 36 for the entire length of cavity 30.

Positioned along groove 36 in spaced relation to one another, are a plurality of electrical contacts 38a–38j. Each contact 38a–38j includes a foot 40 which is press-fitted within groove or channel 36 so as to hold the contacts 38a–38j in place. Each contact 38a–38j is connected to a lead 42a–42j, respectively. The leads 42a–42j may be printed on the floor of cavity 30 or on an insert resting on the floor of cavity 30 if desired. These leads extend upwardly through electrical conduit 34 where they are connected to light indicator assembly 14. As can be seen in FIG. 7, light emitting diodes 44a–44j are connected to each of the respective contacts 38a–38 j.

Mounted over the upper surface of cavity 30 is a diaphragm plate 46 which is constructed of an electrically conductive material, and which has the capability of deflecting inwardly and outwardly with respect to the cavity 30. Attached by gluing or other means to the under surface of diaphragm 46 is a dielectric spacer plate 48 which includes a plurality of circular openings 50a–50j therein. These openings surround each of the contacts 38a–38j, and are substantially larger than the circular size of contacts 38a–38j. The thickness of spacer plate 48 is approximately the same as the height of the contacts 38a–38j so that spacer plate 48 in its normal position such as shown in FIG. 4, permits contacts 38a–38j to come into electrical contact with diaphragm plate 46. As can be seen in FIG. 4, channel 36 provides fluid communication between all of the openings 50a–50j so that the fluid pressure within each of the cavities 50a–50j remains equal. A grounding lead 52 is connected to plate 48 and extends upwardly through electrical conduit 34 along with the electrical leads 42a–42j. Grounding lead 52 is connected in the circuitry with the light emitting diodes 44a–44j and the contacts 38a–38j, as is illustrated in FIG. 7.

In the normal position of the diaphragm plate 46 as shown in FIGS. 3 and 4, all of the contacts 38a–38j are in electrical contact with plate 46, thereby completing the circuitry shown in FIG. 7 and causing light emitting diodes 44a–44j to be lit.

In order to take a measurement with the device, the wedge shaped member 12 is forced into the ground by hydraulic means or other conventional means used for inserting soil testing devices into the soil. Initially, the soil pressure exerted on diaphragm plate 46 keeps all of the contacts 38a–38j in electrical contact with plate 46. The person conducting the test then actuates the pump 54 which forces fluid into cavity 30. The pressure of the fluid within cavity 30 is measured by pressure gauge 16. The pressure within cavity 30 is gradually increased until a bulge is caused in diaphragm plate 46 adjacent the lower end thereof. Referring to FIG. 5, the pressure exerted by the soil on the plate 46 is represented by the vectors S1, S2, S3, etc. The soil pressure adjacent contact 38j is represented by the vector S1; the soil pressure adjacent contact 38i is S2; the soil pressure adjacent contact 38h is S3; and so on. The pressures S1–S10 increase gradually with the lowest pressure being at S1 and the highest pressure being at S10. This is a phenomena which occurs naturally as the result of the wedge shaped configuration of body 12.

The fluid pressure within cavity 30 will cause the diaphragm plate 46 to bulge adjacent contact 38j when the fluid pressure exceeds the soil pressure S1. However, if the fluid pressure within the cavity 30 does not exceed the soil pressure S2, the bulge will occur only adjacent contact 38j. As shown in FIG. 5, the pressure (P2) exceeds the soil pressure S2, thereby causing bulging of plate 46 adjacent both contacts 38i and 38j.

As the bulging occurs, the electrical contact between the contacts 38i and 38j is broken, and the corresponding light emitting diodes go out. The operator gradually increases the pressure within the chamber, and records the fluid pressure within the chamber at the time each light emitting diode 42a–42j goes out. The result is a series of readings shown by points 66a–66j which are on the graph in FIG. 10. These points can be used to plot a straight line designated by the numeral 56, and this straight line can be extended to the Y axis so as to obtain an extrapolation of the pressure which would be achieved with a blade having a theoretical thickness of zero.

A modified form of the invention is shown in FIGS. 8 and 9 and is designated by the numeral 58. Device 58 is identical to device 10 in all respects with the exception that instead of utilizing electrical contacts 38a–38j, device 58 utilizes a plurality of resistance-type strain gauges 60a–60j. These strain gauges each have electrical leads which extend to a meter 62. A rotary switch 64 permits meter 62 to be connected to each of the strain gauges 60a–60j individually so as to attain separate readings for each strain gauge.

With the device shown in FIGS. 8 and 9, it is possible to insert the wedge shaped member 12 into the ground and to read the various pressures exerted on each of the strain gauges 60a–60j, merely by rotating switch 64 into electrical contact with each of the separate strain gauges. The readings on meter 62 are used to plot the points on the graph shown in FIG. 10, and the same results can be obtained as with the use of the device shown in FIGS. 1-6.

The strain gauges utilized for the device shown in FIG. 9 are electrical resistance strain gauges of which many various types are commercially available. An example of a strain gauge which will work in the present invention is a gauge manufactured by Micro Measurements Company, Post Office Box 27777, Raleigh, N.C. 27611, under the Model Number 683JB, or 683JC, or the equivalent thereof. Other types of strain gauges are also commercially available.

The device of the present invention is simple and easy to operate. A number of readings can be obtained by virtue of the plurality of sensors located along the length of the wedge member. Preferably ten sensors may be used, although this may be varied according to the particular needs of the person taking the test. The device does not require a plurality of vanes having different thicknesses as in previous testing devices, and yet it still permits the obtaining of a plurality of readings so as to achieve accurate results.

Thus, it can be seen that the device accomplishes at least all of its stated objectives.

What is claimed is:

1. An in situ soil testing device comprising:
   a tapered body member having an upper end, a lower end, and opposite tapered surfaces each commencing at said upper end and extending downwardly and converging toward one another adjacent said lower end;
   an elongated pressure cavity being formed in one of said tapered surfaces and extending along the length thereof, said cavity having an open upper end presented outwardly away from said one tapered surface;
   flexible diaphragm means attached in covering relation over said open upper end of said cavity to create a substantially fluid tight cover to said cavity;
   a plurality of sensing means positioned in spaced relation to one another within said cavity in a line which extends from a point adjacent said upper end of said body member to a point adjacent said lower end of said body member, each one of said sensing means being capable of individually sensing the soil pressure exerted on said diaphragm adjacent said one sensing means when said tapered body member is buried in the soil;
   indicator means connected to each of said sensing means for indicating the soil pressure sensed by said sensing means;
   fluid conduit means in fluid communication with said cavity;
   a fluid pressure source connected to said conduit means and adapted to introduce selected variable fluid pressures to said cavity through said conduit means;
   said pressure cavity providing fluid communication to all of said pressure sensing means so that all said pressure sensing means are subjected to substantially the same fluid pressure at any one time;
   gauge means for monitoring the fluid pressure within said cavity.

2. An in situ soil testing device according to claim 1, wherein said sensing means comprise a plurality of electrical contacts positioned in spaced relation to one another along the length of said cavity, each of said contacts being in electrical contact with said diaphragm means when said diaphragm means is free from deflection, each one of said contacts being out of electrical contact with said diaphragm when the portion of said diaphragm adjacent said one contact is deflected outwardly in response to elevated fluid pressure within said cavity.

3. An in situ soil testing device according to claim 2 wherein said indicator means comprises a plurality of electric lights, each connected in series to one of said contacts.

4. An in situ soil testing device according to claim 2 wherein said diaphragm means is made of electrically conductive material, electrical power means being connected in parallel to each of said contacts and lights, said diaphragm means being electrically connected to ground so as to complete a circuit to each of said lights when said diaphragm means is in contact with said contacts.

5. An in situ soil testing device according to claim 1 wherein said sensing means comprise a plurality of strain gauges, said indicator means comprising electrical meter means connected to each of said strain gauges.

6. An in situ soil testing device comprising:
   a tapered body member having an upper end, a lower end, and a pair of oppositely facing spaced apart tapered surfaces extending therebetween, the distance between said tapered surfaces being greatest adjacent said upper end and progressively decreasing toward said lower end,
   an elongated cavity being formed in one of said tapered surfaces and extending along the length thereof, said cavity having an open end facing outwardly away from said one tapered surface;
   a plurality of sensing means positioned in spaced apart relation to one another along a line extending longitudinally with respect to one of said tapered surfaces, each one of said sensing means being individually capable of sensing external pressure being exerted on said one tapered surface at a location adjacent said one sensing means;
   a flexible diaphragm plate means positioned in covering relation over said cavity and forming said one tapered surface, and normally having a plurality of contact points, each of which is in contact with one of said sensing means, each one of said contact points of said diaphragm plate means being individually movable in response to increased fluid pressure within said cavity to a level greater than the external pressure on said diaphragm plate means adjacent said one contact point from a normal position in contact with said sensing means to a second position free from contact with said sensing means; and
   indicator means individually connected to each of said sensing means for indicating the pressure exerted by said plate means on said sensing means.

7. An in situ soil testing device according to claim 6 wherein said sensors each comprise a strain gauge.

8. An in situ soil testing device according to claim 1 wherein said cavity includes a bottom floor wall in spaced apart relation to said diaphragm means, said sensing means comprising a plurality of strain sensors positioned between said bottom floor wall and said plate means.

9. A method for testing soil utilizing an elongated tapered body member having opposite tapered surfaces with upper and lower ends, said tapered surfaces converging toward one another at said lower ends, an elongated cavity being formed in at least one of said tapered surfaces and having a flexible diaphragm plate in covering relation over said cavity, said diaphragm plate having upper and lower ends and forming a continuation of said one tapered surface, a plurality of sensor means located within said cavity and normally being in pressure contact with said diaphragm plate, said plurality of sensing means being arranged in a line extending longitudinally with respect to said tapered surfaces, said method comprising:

forcing said tapered body member into the soil to be tested with said lower ends of said tapered surfaces penetrating the deepest into the soil whereby said soil exerts variable pressure on said diaphragm plate with the minimum pressure being exerted on said lower end of said plate and with the soil pressure gradually increasing toward said upper end of said plate;

introducing fluid pressure into said cavity so as to exert an outward pressure on said diaphragm plate from within said cavity, said outward pressure being in opposition to said soil pressure;

gradually increasing said fluid pressure within said cavity until said diaphragm plate deflects outwardly out of contact with the lowermost one of said sensing means;

continuing to gradually increase said fluid pressure within said cavity so as to cause said diaphragm plate to deflect out of contact with said sensing means one at a time commencing from the lowermost of said sensing means and progressing upwardly therefrom;

monitoring the fluid pressure within said cavity at the time that said diaphragm moves out of pressure contact with each of said sensing means.

10. A method according to claim 9 wherein said sensing of said soil pressure by said sensing means is accomplished by a plurality of resistance type strain gauges located along the length of one of said tapered surfaces, said displaying of the sensed soil pressure being accomplished by meter means electrically connected to said strain gauges.

* * * * *